United States Patent [19]

Kaplan

[11] Patent Number: 4,632,935
[45] Date of Patent: Dec. 30, 1986

[54] OMEGA-(HYDROXY-, ETHER AND ESTER)-ALKYL-2-AMINO-CYCLOALKYL- AND CYCLOALKENYL AMIDES AS ANALGESICS

[75] Inventor: Lester J. Kaplan, Irvine, Calif.

[73] Assignee: The Upjohn Company, Kalamazoo, Mich.

[21] Appl. No.: 615,448

[22] Filed: May 30, 1984

[51] Int. Cl.$^4$ .................. A61K 31/40; A61K 31/445; C07D 207/06; C07D 207/20
[52] U.S. Cl. .................................... 514/429; 514/331; 514/210; 514/412; 514/427; 546/234; 548/515; 548/560; 548/565; 548/578; 548/950
[58] Field of Search ............... 548/578, 560, 565, 515; 514/427, 429, 412

[56] References Cited

U.S. PATENT DOCUMENTS

| | | | |
|---|---|---|---|
| 4,065,573 | 12/1977 | Lednicer | 424/278 |
| 4,098,904 | 7/1978 | Szmuszkovicz | 424/324 |
| 4,145,435 | 3/1979 | Szmuszkovicz | 424/274 |
| 4,212,878 | 7/1980 | Lednicer et al. | 424/274 |
| 4,359,476 | 11/1982 | Kaplan et al. | 546/15 X |
| 4,360,531 | 11/1982 | McMillan et al. | 546/15 X |
| 4,438,130 | 3/1984 | Kaplan | 424/274 |
| 4,460,600 | 7/1984 | Kaplan et al. | 546/234 X |
| 4,466,977 | 8/1984 | McMillan et al. | 546/234 X |

Primary Examiner—Joseph Paul Brust
Attorney, Agent, or Firm—John T. Reynolds

[57] ABSTRACT

OMEGA-(Hydroxy, ether and ester) alkyl-2-Amino-Cycloalkenyl and -cycloalkyl amide compounds of the formula:

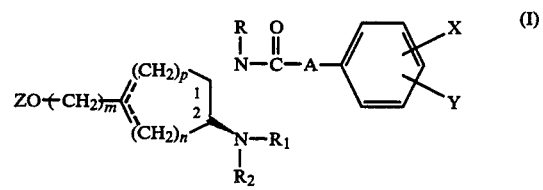

where the wavy line bonds, m, n, p, A, R, $R_1$, $R_2$, X, Y and Z are as defined in the specification, e.g., 3,4-dichloro-N-methyl-N-[2-(1-pyrrolidinyl)-3-(3-acetyloxypropyl)cyclohexenyl]benzamide, and pharmacologically acceptable salts thereof, are useful as analgesic drug compounds having low physical dependence liability, compared to morphine and methadone. Pharmaceutical compositions and methods for using these compounds and compositions as analgesics are disclosed. Processes for preparing this class of compounds are also disclosed.

14 Claims, No Drawings

OMEGA-(HYDROXY-, ETHER AND ESTER)-ALKYL-2-AMINO-CYCLOALKYL- AND CYCLOALKENYL AMIDES AS ANALGESICS

INTRODUCTION

This invention relates to hydroxy-, alkyloxy- and alkanoyloxyalkyl-substituted-2-amino-cycloaliphatic amide compounds, and their use as analgesic drug compounds. More particularly, this invention provides some new 2-amino-omega- (hydroxy-, ether and ester-alkyl)-cycloalkyl and cycloalkenyl-benzeneacetamide and -benzamide compounds which can be used as the active analgesic drug compound in pharmaceutical compositions thereof.

BACKGROUND OF THE INVENTION

Kaplan U.S. Pat. No. 4,438,130 discloses some 1-oxa-, aza- and thia-spirocyclic compounds which are useful as analgesics. That patent also refers to other prior patents which may be of interest to the reader hereof.

Those skilled in the art continue to search for new and more potent or otherwise advantageous chemical compounds which have activity as analgesic drug compounds or for other pharmaceutical use or chemical intermediate purposes.

OBJECTS OF THE INVENTION

It is an object of this invention to provide a series of related 2-amino-(hydroxy-, alkyloxy- and alkanoyloxy-alkyl)cycloaliphatic benzeneacetamide and -benzamide compounds which are useful as analgesic compounds or as chemical intermediates to analgesic compounds.

It is a further object of this invention to provide compositions of the new compounds described herein in combination with a pharmaceutical carrier, which compositions are useful in pharmaceutically effective dosage unit form for alleviating pain in warm-blooded animals, including humans.

Another object of the invention is to provide a method for alleviating pain in a warm-blooded animal, including humans, which comprises administering to such animal suffering pain an amount of a new compound described herein in a pharmaceutically acceptable dosage unit form which is effective in alleviating pain in said animal.

Other objects, aspects and advantages of this invention will become apparent from reading the remaining specification and the claims which follow.

SUMMARY OF THE INVENTION

Briefly, this invention provides a series of related 2-amino(hydroxy-, alkyloxy- and alkanoyloxy-alkyl)-cycloaliphatic)benzeneacetamide and -benzamide compounds, e.g., 3,4-dichloro-N-methyl-N-[2-(1-pyrrolidinyl)-4-(acetyloxypropyl)-3- and 4-cycloalkenyl]-benzeneacetamide, and salts thereof, which have been found to have useful ranges of analgesic properties for use of such compounds in pharmaceutical compositions for treating valuable warm-blooded animals, including humans, when administered by either the oral or parenteral routes to the warm-blooded animal or human patient in need of pain relieving treatment.

This invention also includes compounds of the above general type which may exhibit some analgesic activity of their own, but which are of some importance as chemical intermediates for the preparation of more advantageous analgesic drug compounds included herein. This invention also includes pharmaceutical compositions containing these compounds as an active analgesic component and the method of inducing analgesic activity in the animal patient, including humans, by administering one of these new compounds in an amount effective and sufficient to induce analgesic activity, regardless of origin of the pain, e.g., traumatic pain, bone pain, cancer pain, post-surgical pain, homotropic pain, menstrual pain, headache, and the like. This invention also relates to the use of these new compounds in pharmaceutical dosage unit forms, to be used, hopefully more advantageously, by the oral or parenteral administration route, for the relief of pain in valuable animals and human patients suffering pain. With more potent analgesic compounds, it should be possible to administer less of the compound to obtain a desired degree of relief from pain in the patient.

DETAILED DESCRIPTION OF THE INVENTION

More particularly, this invention provides a group of new N-[2-amino-omega-(hydroxy-, alkyloxy-, and alkanoyloxy-alkyl)cycloalkenyl- and -cycloalkyl]benzeneacetamide and -benzamide compounds, and mixtures thereof, having a new chemical structure I (see GENERAL CHEMICAL STRUCTURE sheets), featuring new hydroxyalkyl-, alkyloxyalkyl- and alkanoyloxyalkyl- substituents on the 2-aminocycloaliphatic ring of the compounds.

In the compounds of Formula I the wavy line bonds between the nitrogens and the cycloaliphatic ring carbon atoms indicate a cis or trans relationship of the two nitrogen-containing groups at positions 1 and 2 of the cycloaliphatic ring.

p is a whole number integer 0, 1, 2, 3, 4 and n is a whole number integer, 0, 1, 2, 3 or 4 so that the resulting cycloaliphatic ring containing p and n has 5, 6 or 7 carbons;

m is 3 or 4;

A is a single chemical bond (—), —(CH$_2$)$_q$— where q is a whole number integer 1 to 4 or —CH(CH$_3$)—;

X and Y are independently selected from the group consisting of hydrogen, a halogen having an atomic number of from 9 to 35, trifluoromethyl, nitro, methoxy, hydroxy, azido, C$_1$ to C$_3$-alkyl, phenyl, methanesulfonyl, cyano, amino, C$_1$ to C$_3$-alkoxycarbonyl, C$_1$ to C$_3$-alkanoyloxy, C$_1$ to C$_3$-carboxyacylamino (—NCH(O)R$_4$ wherein R$_4$ is hydrogen or C$_1$ to C$_2$-alkyl);

R is hydrogen or C$_1$ to C$_3$-alkyl;

R$_1$ and R$_2$, taken separately, are each hydrogen, C$_1$ to C$_3$-alkyl or allyl;

R$_1$ and R$_2$, taken together, with the nitrogen to which they are bonded, complete a ring selected from the group consisting of azetidinyl, pyrrolidinyl, piperidinyl, pyrrolyl, 3-pyrrolin-1-yl

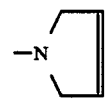

3-azabicyclo[3.1.0]hexan-3-yl
and

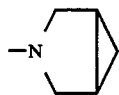

3-azabicyclo[3.2.0]heptan-3-yl

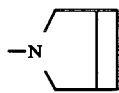

Z is selected from the group consisting of hydrogen, $C_1$ to $C_3$-alkyl and $C_1$ to $C_3$-alkalnoyloxy, and the perforated lines in the cycloaliphatic ring denote the option of a saturated cycloaliphatic ring, and mixed or separated cycloalkenyl ring compounds having the carbon-to-carbon double bond at one of the two indicated positions of that cycloaliphatic ring, or a pharmacological acceptable salt thereof.

Thus, these new compounds contain a hydroxy-$C_3$ to $C_4$-alkyl, $C_1$ to $C_3$-alkyloxy-$C_3$ to $C_4$-alkyl ether group or a $C_1$ to $C_3$-alkanoyloxy-$C_3$ to $C_4$-alkyl ester group substituent on the 3-, 4-, 5-, 6- or 7-position of the cycloaliphatic ring, and an asymmetric carbon atom at such 3-, 4-, 5-, 6- or 7-position which are not found in any straight chained substituted cycloaliphatic ring 2-amino-1-amide compounds of which we are aware.

The compounds of Formula I or their acid addition salts in their crystalline state may sometimes be isolated from their reaction mixtures as solvates, i.e., with a discrete quantity of solvent, e.g., water, ethyl acetate, methanol, and the like, associated physically, and thus not affecting the chemical entity per se.

It will be recognized by those in the organic chemical art that the carbon atoms at positions 1 and 2 of the cycloaliphatic ring or structure (I) to which nitrogens are bonded are asymmetrically substituted. Likewise, the cycloaliphatic ring carbon atom to which the Z—O—$(CH_2)_m$— group is bonded is also asymmetrically substituted. Each of these three cycloaliphatic carbon atoms can independently possess an R or S-configuration and thus a compound of the formula (I) may have as many as $2^3$ or 8 stereoisomers which comprise four parts of enantiomers; each enantiomeric pair is termed a racemate. See, for example, J. B. Henderickson, D. J. Cram and G. S. Hammond, Organic Chemistry, Third Edition, McGraw-Hill Book Company, New York, N.Y., 1970, pp. 198-230, particularly pages 207, 208, 213 and 215. Of the four racemates, two will have the nitrogen-containing groups at positions 1 and 2 of the structure (I) is a trans orientation; that is, the groups will be on opposite sides of the plane of the cycloaliphatic ring; such compounds will be generally referred to in this specification as trans compounds and are meant to include both possible configurations of the third substituted ring carbon. The other two racemates will have the nitrogen-containing groups at positions 1 and 2 of the structure (I) in a cis orientation; that is, the groups will be on the same side of the cycloaliphatic ring; such compounds will be generally referred to in this specification as cis compounds and are meant to include both possible configurations of the third substituted ring carbon atom. The four racemates of structure (I) compounds each exist as a mixture of the two enantiomers of each enantiomer of each pair can be separated by conventional methods. This invention includes within its scope all enantiomeric and diastereomeric forms of the Formula I compounds either impure form or as mixtures of enantiomers or diastereomers. In GENERAL CHEMICAL STRUCTURE I and in CHART A below, when a particular enantiomer or diastereomer or set of enantiomers or diastereomers is illustrated, the intent is only to convey relative stereochemistry. When it is desired to specify for a formula (I) compound the configuration of the other asymmetric centers relative to that of position 1, this is done according to the Chemical Abstracts Service publication, "Naming and Indexing of Chemical Substances for CHEMICAL ABSTRACTS during the Ninth Collective Period (1972-1976)", a reprint of Section IV (Selection of Index Names for Chemical Substances) from the CHEMICAL ABSTRACTS Volume 76 Index Guide. Accordingly, the relative stereochemistry of three asymmetric carbon atoms in the cycloaliphatic ring of Formula I compounds is indicated by: (1) the arbitrary designation of $1\alpha$ for the orientation of the substituent on (asymmetric) carbon atom number one; (2) the designation of $2\alpha$ or $2\beta$ when the substituent on (asymmetric) carbon atom number two is the same or opposite side of the plane of the cycloaliphatic ring, respectively, relative to said $C_1$ substituent; and (3) the designation $x\alpha$ or $x\beta$ when the substituent on (asymmetric) carbon atoms number x is on the same or opposite side of the plane of the cycloaliphatic ring, respectively, relative to said $C_1$ substituent.

When the stereochemistry at carbon atom number x is unknown, the designation $x\xi$ (x Xi) is used to denote either a single epimer or a mixture of epimers at carbon atom x.

Two isomers which differ only in the stereochemistry at one asymmetric carbon atom of the cycloaliphatic ring are sometimes herein referred to as epimers.

If desired the Formula I compounds of this invention can be resolved into their respective d- and l-optical isomers by methods known in the art. In this case, the optical resolution can be done by at least two different routes. The resulting agents by either route are any of the known resolving agents such as optically active camphorsulfonic acid, bis-o-toluyltartaric acid, tartaric acid and diacetyl tartaric acid which are commercially available and which are commonly used for resolution of amines (bases), as for example in Organic Synthesis, Coll. Vol. V, p. 932 (1973), resolution of R-(+) and S-(−)-α-phenylethylamine with (−)-tartaric acid.

By the first method for resolving the compounds of this invention, for example, one of the aminoamide compounds can be converted into its optically active diastereomeric salts by reaction with an optically active acid—examples mentioned above—in a manner standard in the isomer resolution art. These diastereomeric salts can then be separated by convention means such as differential crysallization. Diastereomeric salts have different crystallization properties, which are taken advantage of in this separation. On neutralization of each diastereomeric salt with aqueous base the corresponding active enantiomers of the free aminoamide can be obtained, each of which can subsequently and separately be converted as hereinafter described in the examples to the desired acid addition salt.

By the second method, which in the case of some of these compounds is preferred, the Formula I compounds can be made into their respective d- and l-isomers, by first resolving each cis- or trans-1,2-cycloaliphatic unsymmetrically substituted amino-alcohol or diamine starting material into its respective d- or l-isomers by treatment with the resolving agent, crystallization, separation and regeneration of the respective trans-d-diamine, trans-l-diamine, or the cis-d-diamine and cis-l-diamine, and then reacting the respective resolved diamine starting material with the desired aracyl imidazole (III) or the acyl halide (IV) to form the respective cis- or trans-d- or l-compound of Formula I, which can then be converted to any desired pharmaceutically acceptable acid addition salt by procedures exemplified hereinafter.

In the Formula I compounds, the halogens having atomic numbers of 9 to 35 are fluorine, chlorine and bromine, the term "$C_1$ to $C_3$-alkyl" means methyl, ethyl, n-propyl and isopropyl.

A preferred subgroup of these Formula I compounds are those of Formula I where p is 0, 1 or 2, n is 1, 2 or 3, so that the resulting cycloaliphatic ring containing them has six (6) carbon atoms, m is 3 or 4, A is —$(CH_2)_q$— where q is a whole number integer of from 0 to 1;

X and Y are independently hydrogen or halogen having an atomic number of from 9 to 35;

R is $C_1$ to $C_3$-alkyl;

$R_1$ and $R_2$ are taken together with the nitrogen to which they are bonded to complete a ring selected from the group consisting of azetidinyl, pyrrolidinyl and piperidinyl, and Z is $C_1$ to $C_3$-alkanoyl, or a pharmaceutically acceptable salt thereof.

Examples of such compounds include:

3,4-dichloro-N-methyl[2-(1-pyrrolidinyl)-4-(acetyloxypropyl)-3- and 4-cyclohexenyl]benzeneacetamide, mixed isomers, and 3,4-dichloro-N-methyl-N-[2-(1-pyrrolidinyl)-3-(3-acetyloxypropyl)-3-cyclohexenyl]benzeneacetamide, or a pharmacologically acceptable salt thereof.

Another subgroup of the compounds of this invention are those where p is 0, 1 or 2 and n is 1, 2 or 3 so that the resulting cycloaliphatic ring containing them has six (6) carbon atoms.

m is 3 or 4;

A is —$(CH_2)_q$— where q is a whole number integer of from 0 to 1;

X and Y are independently hydrogen or a halogen having an atomic number of from 9 to 35, R is $C_1$ to $C_3$-alkyl;

$R_1$ and $R_2$ are taken together with the nitrogen to which they are bonded to complete a ring selected from the group consisting of azetidinyl, pyrrolidinyl and piperidinyl; and Z is hydrogen, or a pharmaceutically acceptable salt thereof.

Examples of such compounds include:

3,4-dichloro-N-methyl-N-[2-(1-pyrrolidinyl)-4-(3-hydroxypropyl)-3- and 4-cyclohexenyl]benzeneacetamide mixed isomers, and the respective separated 3- and 4-cyclohexenyl isomers thereof.

Another subgroup of compounds of the above invention are those wherein p is 0, 1 or 2, and n is 1, 2 or 3 so that the resulting cycloaliphatic ring containing them has six (6) carbon atoms, m is 3 or 4;

A is —$(CH_2)_q$— where q is a whole number integer of from 0 to 1;

X and Y are independently hydrogen or a halogen having an atomic number of from 9 to 35;

R is $C_1$ to $C_3$-alkyl;

$R_1$ and $R_2$ are taken together with the nitrogen to which they are bonded to complete a ring selected from the group consisting of azetidinyl, pyrrolidinyl and piperidinyl; and Z is $C_1$ to $C_3$-alkyl, or a pharmacologically acceptable salt thereof.

Examples of such compounds include:

3,4-dichloro-N-methyl-N-[2-(1-pyrrolidinyl)-4-(3-methoxypropyl)-3-cyclohexenyl]benzeneacetamide, 3,4-dichloro-N-methyl-N-[2-(1-pyrrolidinyl)-4-(3-methoxypropyl)cyclohexyl]benzeneacetamide, or a pharmaceutically acceptable salt thereof.

Examples of other compounds within the scope of the invention include:

3,4-dichloro-N-methyl-N-[2-(1-azetidinyl)-3-(3-propionoxypropyl)cyclohexyl]benzeneacetamide, 4-bromo-N-ethyl-N-[2-(1-piperidinyl)-3-(3-formyloxypropyl)-3-cyclohexenyl]benzamide, 3,4-difluoro-N-methyl-N-[2-(1-pyrrolidinyl)-4-(3-ethoxypropyl)-4-cyclohepyl]benzamide, 4-trifluoromethyl-N-ethyl-N-[2-(1-pyrrolidinyl)-3-(3-propyloxypropyl)cyclohexyl]benzeneacetamide, 4-chloro-3-methoxy-N-ethyl-N-[2-(1-azetidinyl)-4-(4-methoxybutyl)-4-cyclohexenyl]benzeneacetamide, 4-azido-N-methyl-N-[2-(1-piperidinyl)-4-(3-acetyloxypropyl)benzeneacetamide, 3,4-dichloro-N-methyl-N-[2-(1-pyrrolidinyl)-4-(4-hydroxypropyl)cyclohept-4-enyl]benzeneacetamide, and the like, and the pharmacologically acceptable salts thereof.

The compounds of this invention can be prepared according to the process shown in chemical flow sheet progression form in CHART A, where the wavy line bonds, m, p, n, A, X, Y, R, $R_1$ and $R_2$ are as defined hereinabove, starting from compounds of Structure II, which compounds (II) are described in Kaplan U.S. Pat. No. 4,438,130.

In Formulas III, IV and V of CHART A, the dashed lines in the cycloaliphatic ring indicate the presence of one double bond at either of the two indicated adjacent positions in the cycloaliphatic ring to make the ring a cycloalkenyl ring having the Z—O—$(CH_2)_m$— group bonded to a cycloaliphatic ring carbon atom to which said double bond is attached.

In the processes for making the compounds of this invention, described herein, care should be taken that functional groups, i.e., groups of the overall molecule which are to be retained in the end product Structure I compound, are not undesirably changed under the reaction conditions used. Where such functional group alteration may be a concern to the chemist, it may be advantageous to use known protecting group methodology to protect desired groups while other selective reactions are conducted.

Referring to CHART A, for a depiction of the various process steps which can be used to prepare the compounds described herein, (I) the starting material compound II is reacted with a mixture of a mineral acid such as sulfuric acid, hydrochloric acid, orthophosphoric acid, p-toluenesulfonic acid, or the like, preferably sulfuric acid, and a carboxylic acid, preferably a $C_1$ to $C_3$-alkanoic acid such as formic, acetic, m-propionic, isopropanoic acid so as to form the first group of desired new alkanoyloxyalkyl-substituted cycloaliphatic compounds of this invention. Preferably acetic acid is used in a volume/volume ratio range of from about 0.5 to 3:1 to 3 of the mineral acid to carboxylic acid solutions, respectively. Concentrations of the respective acids can range from 0.1 to about 36N, whatever are the normal laboratory reagent acid concentrations.

The mixture of the Formula II compound in the mixed mineral/carboxylic acid mixture is heated to elevated temperatures, e.g., to from about 60° C. to 120° C., preferably to about 90° C., for a time sufficient to form the mixed isomer ring-double bond, ring-opened compound of Formula III, where $R_4$ is the residue of the carboxylic acid used, preferably hydrogen or $C_1$ to $C_2$-alkyl. Usually, this ring opening reaction on most Formula II compounds is essentially complete in about two hours, although for some combinations of Formula II starting materials and mixed acids longer reaction times up to 24 hours may be desirable to effect essentially complete ring opening reaction.

The resulting first intermediate (III), the alkanoyloxyalkyl ester compounds (III) can then be handled or treated in either of two ways, as shown on CHART A. The unsaturated cycloaliphatic ester intermediate (III) can be saponified by known procedures with a basic solution to remove the alkanoyl group to form the ring unsaturated alcohol compound (IV). In our preferred method, the ester compound (III) is saponified with a base in a suitable solvent, e.g., with 10% weight/volume sodium hydroxide in water solution in an alkanol, preferably methanol, preferably in a V/V ration of about 1:5, base solution, alcohol, respectively, at atmospheric temperature, which is usually about 18° C. to 25° C., for a time sufficient to form the alcohol compound (IV). This reaction is usually complete in about 0.5 hour with preferred reactants. Other combinations of reactants may take longer reaction times.

In this process flow path, the ring unsaturated alcohol (IV) can be recovered and used as such as an analgesic drug compound or used further in the next step of the process as a chemical intermediate to form the ring unsaturated $C_1$ to $C_3$-alkyl ether derivatives (IX) of this invention, where $R_6$ is the $C_1$ to $C_3$-alkyl ether group. Our preferred process for so using the alcohol (IV) with an activating group compound such as a sulfonic acid, e.g., a $C_1$ to $C_6$-alkanesulfonic acid or halide, e.g., with methanesulfonic acid or chloride, in the presence of an acid scavenging base such as a tertiary amine, e.g., triethylamine, in a suitable solvent such as a halogenated hydrocarbon such as methylene chloride, chloroform, carbon tetrachloride, ethylene polychloride, preferably a methylene chloride containing solvent at a cold temperature, e.g., at about 0° C. to form the corresponding sulfonate ester intermediate (V) where $R_5$ is the residue of the sulfonic acid, preferably a $C_1$ to $C_5$-alkyl or p-toluyl. We prefer to use methanesulfonyl chloride to form the methanesulfonyl ester. The resulting ring unsaturated sulfonyl ester (V) is reacted with the selected metal -$C_1$ to $C_3$-alkoxide, preferably an alkali metal -$C_1$ to $C_3$-alkoxide, e.g., sodium methoxide, in the corresponding $C_1$ to $C_3$-alkanol as solvent at up to reflux temperature of the mixture for a time sufficient to form the $C_1$ to $C_3$-alkyl ether cycloaliphatic ring unsaturated compound (IX). Reaction times in the range of 65 hours or longer under reflux of the reaction mixture conditions are not unusual to ensure essentially complete reaction to form the desired ether compound (IX).

Alternatively, the alkanoyloxy cycloaliphatic ring unsubstituted ester reactant (III) can be catalytically hydrogenated by known process procedures, e.g., with platinum oxide catalyst in ethanol solvent under hydrogen pressure of from 1 to 10 atmospheres to produce the corresponding ring-saturated ester (VI). The saturated ester (VI) can then be treated as described above to saponify the ring saturated alkanoyl ester (VI) to form the corresponding ring-saturated alcohol (VII), which alcohol is then treated, as described above, with a sulfonating agent, e.g., with methanesulfonyl chloride in the presence of a base, e.g., a tertiary amine to form the corresponding sulfonate intermediate, which sulfonated intermediate is then treated with the metal $C_1$ to $C_3$-alkoxide in the corresponding $C_1$ to $C_3$-alkanol solvent to form the respective ring-saturated $C_1$ to $C_3$-alkyl ether compound (VIII).

Also available as an option is to catalytically hydrogenate the double bond of the cycloaliphatic ring unsaturated alkanol compound (IV) or the $C_1$ to $C_3$-alkyl ether (IX) to form the corresponding ring saturated alcohol compound (VII) and $C_1$ to $C_3$-alkyl ether compound (VIII), respectively.

The new alcohol compounds of this invention, i.e., the cycloaliphatic ring unsaturated alcohols (IV) and the cycloaliphatic ring saturated alcohols (VII) can also be used as chemical intermediates to make any desired ester therefrom, e.g., they can be reacted with a reactive form of a $C_1$ to $C_3$-alkanoic acid by known esterification procedures to produce the corresponding new and different $C_1$ to $C_3$-alkanoyl oxyalkyl ester compounds (III) or (VI).

Kaplan U.S. Pat. No. 4,438,130 is incorporated herein by reference thereto for procedures for preparing the starting materials of Formula II herein.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvents, non-aqueous media such as diethyl ether, ethyl acetate and the like. Non-aqueous media are preferred. Also, whereas oxalic acid and other equivalent acids can be used to produce the aminoamide product in a more easily handled solid form, e.g., inplant manufacturing isolation procedures, it would preferably not be used as a pharmaceutically acceptable salt form of the amino-amide product.

This invention also includes compositions useful in pharmaceutically dosage unit form for alleviating pain in warm-blooded animals, including humans, which comprises a compound of Formula I, hereinabove in combination with a pharmaceutically acceptable carrier, a preferred example of these new compounds for this analgesic use is 3,4-dichloro-N-methyl-N-[2-(1-pyrrolidinyl)-3-(3-acetyloxypropyl)-3-cyclohexenyl]benzeneacetamide.

This invention also provides a method or process for alleviating pain in a warm-blooded animal which comprises administering to an animal suffering pain, including a human suffering pain, an effective amount of a compound of Formula I hereinabove in a pharmaceutical dosage unit form. Our preferred example for use in this method or process is 3,4-dichloro-N-methyl-N-[2-

(1-pyrrolidinyl)-3-(3-acetyloxypropyl)-3-cyclohexenyl]benzeneacetamide.

The term "dosage unit form" as used in this specification and in the claims refers to physically discrete units suitable as unitary dosages for mammalian subjects, each unit containing as the essential active ingredient a predetermined quantity of a compound of this invention with the required pharmaceutical means which adapt said ingredient for systematic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, those being features of the present invention. Examples of suitable dosage unit forms in accordance with the invention are tablets, capsules, orally administered liquid preparations in suitable liquid vehicles, sterile preparations in suitable liquid vehicles for intramuscular and intravenous administration, suppositories and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like, and also calcium stearate. Liquid preparations for oral administration are prepared in water or aqueous vehicles which advantageously contain suspending agents, for example methyl cellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the principal solvent or suspending liquid, preservatives in the nature of bacteriostatic and fungistatic agents, for example, parabens, chlorobutanol, benzyl alcohol, phenol, thimerosal and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol and the like. Any solid preparations for subsequent extemporaneous preparation of sterile injectable preparations are sterilized, preferably by exposure to a sterlizing gas, for example, ethylene oxide. The aforesaid carriers, vehicles, diluents, excipients, preservative, isotonic agents and the like constitute the pharmaceutical means which adapt the preparations for systemic administration.

The pharmaceutical dosage unit forms of the compounds of this invention are prepared in accordance with the preceding general description to provide from about 0.5 to about 350 mg. of the essential active ingredient per dosage unit form, which as aforesaid, may be in the form of a semi-solid or solid, topical, oral or rectal preparation, a liquid oral preparation, an injectable preparation including liquid preprations and solid dry preparations for extemporaneous reconstitution to a liquid injectable preparation. The amount of the essential active ingredient provided in the pharmaceutical dosage unit forms is that amount sufficient to obtain analgesic effects within the aforesaid effective non-toxic range. Expressed otherwise, when used systemically, an amount of the essential active ingredient is provided to a recipient within a range from about 0.01 mg./kg. to about 5 mg./kg. of body weight of the recipient.

Preferred dosages for most applications are 0.05 to 2.0 mg./kg. of body weight. In a topical semi-solid ointment formulation the concentration of the active ingredient may be 0.2–10%, preferably 0.5–5% in a carrier, such as a pharmaceutical cream base.

The useful pharmaceutical dosage unit forms of these compounds in a pharmaceutical formulation are preferably adapted for systemic administration to obtain analgesic effects comprising an effective, non-toxic amount of a compound according to Formula I or as its pharmaceutically acceptable salt.

Further, the invention relates to methods of obtaining analgesic effects in mammals, for example, humans and valuable warm-blooded animals such as dogs, cats, horses and other commercially valuable animals, by administering systemically to the mammals the aforesaid pharmaceutical dosage unit forms supplying an effective, non-toxic amount for analgesic effects. These preferred compounds have an advantage, to a greater extent, depending upon the particular compound, of having lower physical dependence liability than known analgesic compounds such as morphine and methadone, as shown by evaluation of representative compounds and those standard analgesic drug compounds in various pharmacological test procedures which measure analgesia and the physical dependence liability of the test compounds in standard laboratory test animals.

Representative examples of these Formula I compounds have $ED_{50}$ values of less than about 75 mg./kg. s.c. (subcutaneous administration) in standard laboratory animal analgesic tests such as the tail flick, pinch, and hydrochloric acid or air writhing tests, and the more potent of them have $ED_{50}$ values of less than 10 mg./kg. (s.c.) in these tests, while at the same time giving quite high values (greater than 250 mg./kg. (s.c.) in the naloxone jumping test thus possessing low apparent physical dependence liability as compared to commercial analgesics used as standards. The procedures used to determine these properties of these new compounds were essentially those of Way et al., (Way, E. L. et al, "Simultaneous Quantitative Assessment of Morphine Tolerance and Physical Dependence", J. Pharmacol. Exp. Ther., 167, pp. 1–8 (1969) and Saelens et al., (Saelens, J. K. et al., "The Mouse Jumping Test—A Simple Screening Method to Estimate the Physical Dependence Capacity of Analgesics", Arch. Int. Pharmacodyn, 190, pp. 213–218 (1971)). Statistically effective doses ($ED_{50}$ values) and 95% confidence limits were calculated by the method of Spearman and Karber (Finney, D. J., "Statistical Methods of Biological Assay", Hafner Publ. (1952)).

For example, representative preferred compounds of Formula I give low analgesic $ED_{50}$ values (less than about 10 mg. of test compound/kg. of animal body weight, subcutaneous administration route) in standard laboratory animal tests while at the same time possessing quite high $ED_{50}$ values (greater than 250 mg./kg. s.c.) in the naloxone jumping test, evidencing substantial freedom from apparent physical dependence liability. In contrast, known analgesic drugs such as morphine and methadone exhibit analgesic $ED_{50}$ values of less than 2 mg./kg. s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg./kg. s.c. Other representative compounds of this invention have analgesic potencies somewhat less than the preferred compounds (analgesic activity $ED_{50}$ values up to about 75 mg./kg. s.c. in these standard tests), and some such compounds are characterized by having only low to moderate apparent physical dependence liability.

This invention is further exemplified by the following detailed examples, the procedures of which can be followed to prepare the compounds of this invention, but these examples are not intended to limit the scope of the invention.

EXAMPLE 1

3,4-Dichloro-N-methyl-N-[2(1-pyrrolidinyl)-4-(acetyloxypropyl)-3- and 4-cyclohexenyl]benzeneacetamide, and their methanesulfonate salts To a solution of 3,4 g. (6.5 millimoles) of $(\pm)$-$(5\alpha,7\alpha,8\beta)$-3,4-dichloro-N-methyl-N-[7-(1-pyrrolidinyl)-1-oxaspiro[4.5]dec-8-yl]benzeneacetamide methanesulfonate salt in 30 ml. of glacial acetic acid there was added 9 ml. of concentrated sulfuric acid. The resulting reaction mixture was stirred at 60° C. for 28 hours, at which time a thin layer chromatographic (TLC) analysis of the reaction mixture showed only a trace of starting materials and three new products. The reaction mixture was stirred at ambient temperature for another 16 hours to ensure complete reaction and then diluted into 500 ml. of ice water. The aqueous solution was made basic with aqueous 45% sodium hydroxide solution, keeping the mixture ice cold. The resulting emulsion was extracted twice with methylene chloride. The combined organic liquid phases were washed with brine solution, dried with magnesium sulfate and the solvent removed leaving 2.9 g. of crude product mixture as a yellow oil.

The crude product oil was chromatographed on 375 g. of Neutral Act. I Alumina (gravity grade) chromatography material, eluting the chromatography column contents therefrom with chloroform, collecting 35 ml. fraction at a flow of 5 ml./minute. All fractions were mixed and were recombined to give 2.0 g. of a purified light yellow oil product. The light yellow oil product from the alumina chromatography column was then chromatographed on about 175 g. of silica gel, eluting the chromatography column contents therefrom with a 3.4% V/V methanol and 10% V/V ammonium hydroxide in ethyl acetate eluting liquid mixture, collecting 30 ml. fractions at a flow rate of 4.3 ml./minutes.

One isomer of the product (spot A) was collected from fractions 50 to 53, 0.25 g. Fractions 54 to 73 gave a three-spot (BCD) mixture product. More pure quantities of the second isomer (spot D) was obtained from fractions 73 to 81, 0.50 g.

The second product, spot D material, 0.50 g., was converted to its methanesulfonate salt, 330 mg., m.p. 178°–181° C., which was recrystallized from a methanol/diethyl ether mixture to give a product, spot D, 3,4-dichloro-N-methyl-N-[2-(1-pyrrolidinyl)-4-acetyloxypropyl)-3- or 4-cyclohexenyl]benzeneacetamide methanesulfonate salt.

Analysis Calcd. for $C_{24}H_{32}Cl_2N_2O_3 \cdot C_4O_3S$: % calcd.: C, 53.28; H, 6.44; N, 4.92; Cl, 12.58; S, 5.90; % found: C, 53.39; H, 6.50; N, 5.09; Cl, 12.77; S, 5.45.

EXAMPLE 2

3,4-Dichloro-N-methyl-N-[2-(1-pyrrolidinyl)-4-(acetyloxypropyl)-3-cyclohexenyl]benzeneacetamide hydrobromide salt To a solution of 10.0 g., (19.1 millimoles) of $(\pm)$-$(5\alpha,7\alpha,8\beta)$-3,4-dichloro-N-methyl-N-[7-(1-pyrrolidinyl)-1-oxaspiro[4.5]dec-8-yl]benzeneacetamide methanesulfonate salt in 90 ml. of acetic acid there was added 30 ml. of concentrated sulfuric acid and the reaction was stirred at 90° C. and monitored by TLC analyses. The TLC sample aliquot of the reaction mixture at 2 hours showed no starting material and one major and one minor product spot. The reaction mixture was poured into 500 ml. of ice/water mixture. The resulting solution was carefully treated with solid sodium bicarbonate to neutralize the bulk of the acetic acid in the mixture and then with 50% sodium hydroxide in water solution, while the flask was cooled in ice, to bring the pH of the resulting mixture to about 13. The resulting emulsion was extracted with three-300 ml. portions of methylene chloride. The combined organic liquid phases were washed with water and dried with magnesium sulfate, and the solvent was removed to leave 7.9 g. of a yellow oil, a sample of which was submitted for Nuclear Magnetic Resonance Spectral (NMR) analysis.

The remainder of the crude yellow oil product was chromatographed through about 400 g. of silica gel, eluting with 4% methanol V/V-10% ammonia V/V in ethyl acetate mixture, collecting 45 ml. fractions at a flow rate of 5 ml./minute. (Note: An apparent plug in the chromatograph column developed overnight, slowing the flow rate.)

Fractions 33–55 contained a TLC spot, (A) compound, 0.64 g. Fractions 67–129 contained a TLC spot, (C) compound, 3.8 .g. Fractions 56–68, mixed TLC the spot material, were discarded.

A portion of the spot A compound was treated with diethyl ether solution of hydrogen bromide to effect precipitation of the hydrogen bromide salt, which was collected and recrystallized from an isopropanol/diethyl ether mixture to obtain the titled compound, m.p. 90°–106° C., bubbling.

Anal. calcd. for $C_{24}H_{32}Cl_2N_2O_3 \cdot HBr$: % calcd.: C, 52.56; H, 6.06; N, 5.11; % found: C, 52.60; H, 6.39; N, 4.79.

EXAMPLE 3

3,4-Dichloro-N-methyl-N-[2-(1-pyrrolidinyl)-4-(3-hydroxypropyl)-3- and 4-cyclohexenyl]benzeneacetamide To a solution of 3.1 g. (6.6 millimoles) of the 3,4-dichloro-N-methyl-N-[2-(1-pyrrolidinyl)-4-(3-acetyloxypropyl)-4-cyclohexenyl]benzeneacetamide (spot C material, Example 2), in 100 ml. of methanol there was added 25 ml. of 10% W/V sodium hydroxide in water solution and the resulting solution was stirred at room temperature for 2 hours, at which time a TLC analysis of a sample of the reaction mixture showed no starting material. The bulk of the methanol diluent/solvent was removed on a rotary evaporator and the residue was distributed between ethyl acetate and water. The aqueous portion of the mixture was separated and extracted with ethyl acetate. The combined ethyl acetate liquid phases were washed with brine solution and dried over magnesium sulfate and the solvent was removed leaving 2.77 g. of crude, title product as a yellow oil.

The crude oil product was flash chromatographed on silica gel, eluting with 0.5:4.5:95, ammonia:methanol:ethyl acetate (V:V:V), collecting 100 milliliter fractions. Fractions 6 to 10 were combined to give substantially pure product, titled above, as a colorless oil. Fraction 5 was mixed TLC ABC spot material and discarded.

The chromatographed oil was recrystallized from a minimum volume of boiling acetonitrile to give two crops of the titled compound:
First crop: 1.1 g.; m.p. 91°–93° C.
Second crop: 0.5 g.; m.p. 90°–93° C.
Anal. calcd. for $C_{22}H_{30}Cl_2N_2O_2$: % calcd: C, 62.11; H, 7.11; N, 6.59; % found: C, 62.03; H, 7.21; N, 6.57.

EXAMPLE 4

3,4-Dichloro-N-methyl-N-[2-(1-pyrrolidinyl)-4-(3-acetyloxypropyl)cyclohexyl]benzeneacetamide A. 3,4-Dichloro-N-methyl-N-[2-(1-pyrrolidinyl)-3- and 4-cyclohexenyl]benzeneacetamide To a solution of 10.0 g. (19.1 millimoles) of (±)-(5α,7α,8β)-3,4-dichloro-N-methyl-N-[7-(1-pyrrolidinyl)-1-oxaspiro[4.5]dec-8-yl]benzeneacetamide methanesulfonate salt in 90 ml. of acetic acid there was added 30 ml. of concentrated sulfuric acid. The resulting mixture was heated at 90° C. and monitored by TLC and NMR analysis of samples of the reaction mixture. After 0.5 hour an aliquot sample still showed some starting material. Heating was continued for an additional 1 hour at which time TLC analysis showed no starting material remaining. The resulting reaction mixture was poured into 1 liter of ice/water mixture and neutralized by careful addition of solid sodium bicarbonate. The pH was adjusted to pH 9 with 10% W/V sodium hydroxide in water solution and the resulting emulsion was extracted twice with 1 liter portions of ethyl acetate. The combined organic liquid phase was washed with brine solution, dried with magnesium sulfate and the solvent was removed leaving 10.1 g. of a yellow oil product.

The crude yellow oil product was chromatographed on about 405 g. of silica gel, eluting with 0.35:3.15:96.5, ammonia:methanol:ethyl acetate (V:V:V), collecting 45 ml. fractions at a flow rate of 5.6 ml./minute after a forerun of 500 ml. (Note: a 50 g. silica gel pre-column was used for the first one liter and then removed). Fractions 30–49 yielded 0.80 g. (spot A) of the 3,4-dichloro-N-methyl-N-[2-(1-pyrrolidinyl)-4-cyclohexenyl]benzeneacetamide. Fractions 57–95 yielded 4.15 g. (spot C) of 3,4-dichloro-N-methyl-[2-(1-pyrrolidinyl)-4-(3-acetyloxypropyl)-3-cyclohexenyl]benzeneacetamide.

B. The titled . . . cyclohexyl compound

To a solution of 1.0 g. (2.14 mmoles) of the above spot C intermediate in 75 ml. of absolute ethanol there was added 50 mg. of platinum oxide. The mixture was placed in and shaken in a Parr apparatus for 20 minutes under 20 psig. of hydrogen. A TLC analysis of the reaction mixture showed only a trace of the starting material. The reaction mixture was filtered and the filtrate was evaporated to leave 0.95 g. of a crude colorless oil product.

The crude oil product was chromatographed on about 50 g. of silica gel eluting with 0.2:1.8:98, ammonia:methanol:ethyl acetate (V:V:V), collecting about 11 ml. fractions, at a flow rate of 3 ml./minute.

Fractions 30 to 56 were combined to give 0.52 g. of a light yellow oil product. This chromatographed product was treated with methanesulfonic acid and the resulting salt precipitate was recrystallized from a methanol/diethyl ether mixture to give 0.38 g. the titled . . . cyclohexane derivative product, m.p. 168°–170° C.

EXAMPLE 5

1,2 3,4-Dichloro-N-methyl-N-[2-(1-pyrrolidinyl)-4-(3-methoxypropyl)-3-cyclohexenyl]benzeneacetamide A. 3,4-Dichloro-N-methyl-N-[2-(1-pyrrolidinyl)-4-(3-hydroxypropyl)-3- and 4-cyclohexenyl]benzeneacetamide To a solution of 1.6 g. (3.4 millimoles) of the 3,4-dichloro-N-methyl-N-[2-(1-pyrrolidinyl)-4-(3-acetyloxypropyl)-3-cyclohexenyl]benzeneacetamide (spot C) from Example 4, part A, in 50 ml. of methanol there was added 10 ml. of 10% W/V/ sodium hydroxide in water solution. The resulting mixture was stirred at room temperature for 1 hour. The bulk of the methanol was removed in a rotary evaporator apparatus and the residue was distributed between ethyl acetate and water phases. The aqueous phase was separated and extracted once with ethyl acetate. The ethyl acetate extracts and phase were combined and washed with brine solution, dried with magnesium sulfate and the solvent was removed leaving 1.4 g. of a light yellow oil product.

The crude yellow oil product was dissolved in about 20 ml. of boiling acetonitrile to form the subtitled 4-(3-hydroxypropyl)-compound. The solution was cooled to room temperature and seeded with some of the same product from a prior run and set aside at −10° C. to allow the product to crystallize out. A 1.0 g. crop of the subtitled product, m.p. 91°–93° C. was obtained.

The mother liquors, after separation of the above crystals, were combined with those of the above referenced previous run.

B. The 4-(3-methoxypropyl)-ether

To a solution of 2.7 g. (6.37 millimoles) of the subtitled 4-(3-hydroxypropyl)-compound, prepared as described in part A above, a 1.0 ml. (7 millimoles) of triethylamine in 25 ml. of methylene chloride, cooled to 0° C., there was added a solution of 0.8 g. (7.0 millimoles) of methanesulfonyl chloride (in methylene chloride) dropwise from an addition funnel. After this addition was complete the resulting reaction mixture was stirred at 0° C. for 0.5 hour at which time a TLC analysis of the reaction mixture showed no starting material was present. The reaction mixture was distributed between methylene chloride and water phases. The aqueous phase was separated and extracted once with methylene chloride. The combined methylene chloride phases were washed with brine solution, dried with magnesium sulfate and the solvent was removed to leave as residue 3.0 g. of the methanesulfonate (mesylate) intermediate, a yellow oil.

The crude mesylate oil was dissolved in 100 ml. of dry methanol and then 0.69 g. (12.7 millimoles) of sodium methoxide was added. The resulting mixture was then refluxed for 64 hours. The bulk of the methanol was removed on a rotary evaporator and then the residue was distributed between ethyl acetate and water. The aqueous phase was separated and extracted once with ethyl acetate. The combined ethyl acetate liquid phases were combined and washed with brine solution, dried over magnesium sulfate and the solvent removed to leave 2.6 g. of the above titled 4-(3-methoxypropyl)ether product as a yellow oil.

The crude yellow oil ether product was chromatographed on a chromatography grade alumina (Acti II), eluting with a 3:1 hexane ethyl acetate (V:V) to give 1.55 g. of the above-titled 4-(3-methoxypropyl)-ether compound as a colorless oil. The structure was confirmed by NMR spectral analysis.

A 0.5 g. portion of this above-named ether oil product was treated with a hydrogen bromide in diethyl ether solution causing formation of a gum salt material. This gum salt material was recrystallized twice from an acetone/diethyl ether mixture to 0.37 g. of the titled ether product as white prism crystals, m.p., 126°-128° C.

Anal. calcd. for $C_{23}H_{32}Cl_2N_2O_2.HBr.0.5H_2O$: % calcd.: C, 52.18; H, 6.47; % found: C, 51.92; H, 6.23.

EXAMPLE 6

3,4-Dichloro-N-methyl-N-[2-(1-pyrrolidinyl)-4-(3-methoxypropyl)cyclohexyl]benzeneacetamide, and its mesylate salt To a solution of 0.90 g. (2.05 millimoles) of the titled 4-(3-methoxypropyl)cyclohexenyl . . . product from Example 5, hereinabove, in 100 ml. of absolute ethanol there was added 50 mg. of platinum oxide ($PtO_2$) and the mixture was shaken on a Parr apparatus under a hydrogen pressure of 30 psig. for 1 hour. After that time, a TLC analysis of a sample of the reaction mixture showed a trace of starting material. To ensure completion of the reaction the reaction mixture was shaken for an additional 2.5 hours under 30 psig hydrogen pressure. The catalyst ($PtO_2$) was removed from the resulting reaction mixture by filtration through a filter aid pad ("Celite TM") and the filtrate was evaporated to leave as residue 0.9 g. of a light yellow oil. A sample of this oil residue product was sent for NMR analysis. The remaining crude product was dissolved in dry diethyl ether and treated with a methanesulfonic acid in diethyl ether solution. A precipitate which formed was collected and washed with diethyl ether. The precipitate was crystallized from a methanol-diethyl ether mixture to give 0.54 g. of the titled compound, as its mesylate salt, m.p., 172°-173.5° C.

EXAMPLE 7

3,4-Dichloro-N-methyl-N-[2-(1-pyrrolidinyl)-4-(3-hydroxypropyl)cyclohexyl]benzeneacetamide, and its mesylate salt To a solution of 0.65 g. (1.53 millimoles) of 3,4-dichloro-N-methyl-N-[2-(1-pyrrolidinyl)-4-(3-hydroxypropyl)-3- and 4-cyclohexenyl]benzeneacetamide (See Example 3 above), in 70 ml. of absolute ethanol there was added 50 mg. of platinum oxide ($PtO_2$). the resulting mixture was shaken on a Parr apparatus under 30 psig. of hydrogen. After 1.5 hours a TLC analysis of a sample of the reaction mixture showed no starting material. The reaction mixture was filtered through a filter and pad ("Celite TM") to separate the solid catalyst and the filtrate was evaporated leaving 0.65 g. of the above-named cyclohexyl compound as a light yellow oil. A sample was taken for NMR analysis.

The remainder of the crude oil product was treated with methanesulfonic acid in diethyl ether solution and the resulting sticky precipitate was collected and crystallized from a methanol/diethyl ether mixture at room temperature to give 0.45 g. of the titled . . . cyclohexyl . . . compound, m.p., 176°-190° C.

GENERAL CHEMICAL STRUCTURES

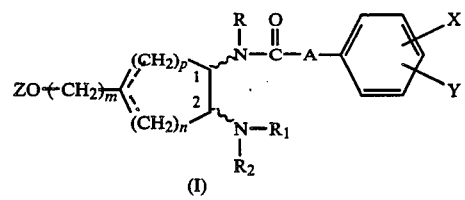

CHART A

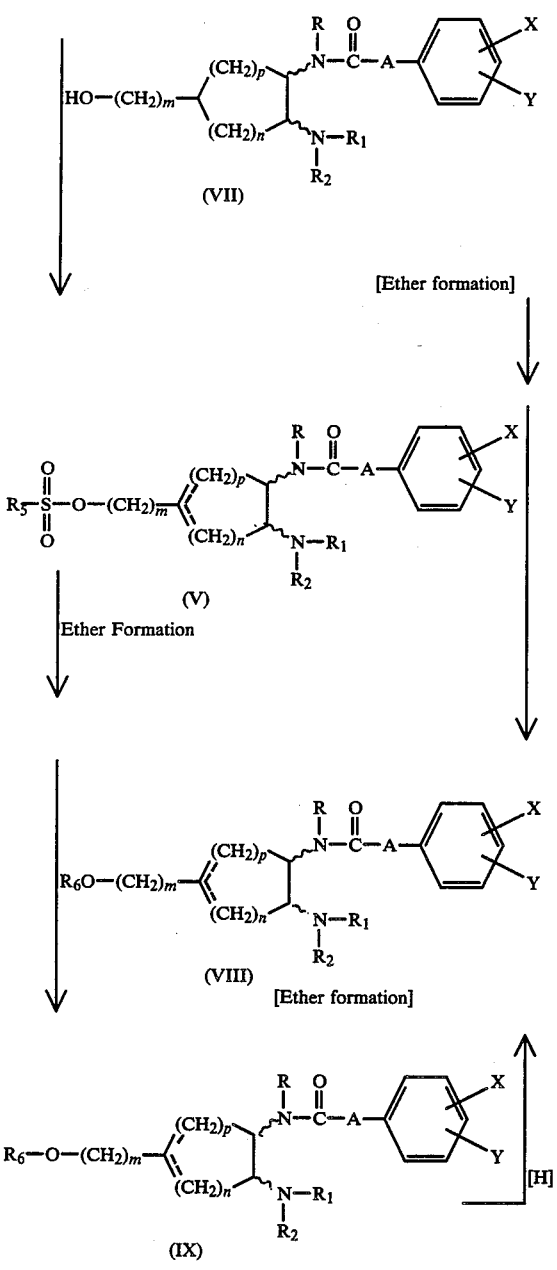

[Ether formation]

Ether Formation

[Ether formation]

[H]

I claim:
1. A compound of the formula

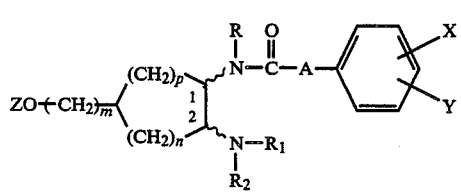

where p is a whole number integer, 0, 1, 2, 3 or 4 and n is a whole number integer 0, 1, 2, 3 or 4, so that the resulting cycloaliphatic ring containing them has 5, 6 or 7 carbon atoms;
m is 3 or 4;

A is —$(CH_2)_q$ where q is a whole number integer 0 to 4 or —$CH(CH_3)$—;

X and Y are independently selected from the group consisting of hydrogen, a halogen having an atomic number of from 9 to 35, trifluoromethyl, nitro, methoxy, hydroxy, azido, $C_1$ to $C_3$-alkyl, phenyl, methanesulfonyl, cyano, —$NH_2$, $C_1$ to $C_3$-alkoxycarbonyl, $C_1$ to $C_3$-alkanoyloxy and $C_1$ to $C_3$-carboxyacylamino;

R is hydrogen or $C_1$ to $C_3$-alkyl;

$R_1$ and $R_2$, taken together with the nitrogen to which they are bonded complete a ring selected from the group consisting of pyrrolidinyl, pyrrolyl, 3-pyrrolinyl, 3-azabicyclo[3.1.0]-hexan-3-yl and 3-azabicyclo[3.2.0]heptan-3-yl;

Z is selected from the group consisting of hydrogen, $C_1$ to $C_3$-alkyl, and
$C_1$ to $C_3$-alkanoyl,
and perforated lines in the cycloaliphatic ring denote the option of a saturated cycloaliphatic ring, and mixed or separated cycloalkenyl rings at one of the two indicated positions of that cycloaliphatic ring; or a pharmaceutically acceptable salt thereof.

2. A compound according to claim 1 wherein p is 0, 1 or 2, n is 1, 2 or 3 so that the resulting cycloaliphatic ring containing them has six carbon atoms,
m is 3 or 4;
A is —$(CH_2)_q$— where q is a whole number integer of from 0 to 1;
X and Y are independently hydrogen or halogen having an atomic number of from 9 to 35;
R is $C_1$ to $C_3$-alkyl;
$R_1$ and $R_2$ are taken together with the nitrogen to which they are bonded to complete a pyrrolidinyl ring;
Z is $C_1$ to $C_3$-alkanoyl, or a pharmacologically acceptable salt thereof.

3. A compound according to claim 2 which is 3,4-dichloro-N-methyl-N-[2-(pyrrolidinyl)-4-(acetyloxypropyl)-3- and 4-cyclohexenyl]benzeneacetamide, mixed isomers, or a pharmacologically acceptable salt thereof.

4. A compound according to claim 3 wherein the compound is 3,4-dichloro-N-methyl-N[2-(1-pyrrolidinyl)-3-(3-acetyloxypropyl)-3-cyclohexenyl]benzeneacetamide, or a pharmacologically acceptable salt thereof.

5. A compound according to claim 1 wherein p is 0, 1 or 2, and n is 1, 2 or 3 so that the resulting cycloaliphatic ring containing them has six carbon atoms,
m is 3 or 4;
A is —$(CH_2)_q$— where q is a whole number integer of from 0 to 1;
X and Y are independently hydrogen or a halogen having an atomic number of from 9 to 35;
R is $C_1$ to $C_3$-alkyl;
$R_1$ and $R_2$ are taken together with the nitrogen to which they are bonded to complete a pyrrolidinyl ring;
Z is hydrogen; or a pharmacologically acceptable salt thereof.

6. A compound according to claim 5 which is 3,4-dichloro-N-methyl-N-[2-(1-pyrrolidinyl)-4-(3-hydroxypropyl)-3- and 4-cyclohexenyl]benzeneacetamide, mixed isomers, or a pharmacologically acceptable salt thereof.

7. A compound according to claim 1 wherein p is 0, 1 or 2 and n is 1, 2 or 3 so that the resulting cycloaliphatic ring containing them has six carbon atoms;

m is 3 or 4;

A is —(CH$_2$)$_q$— where q is a whole number integer of from 0 to 1;

X and Y are independently hydrogen or a halogen having an atomic number of from 9 to 35;

R is C$_1$ to C$_3$-alkyl;

R$_1$ and R$_2$ are taken together with the nitrogen to which they are bonded to complete a pyrrolidinyl ring;

Z is C$_1$ to C$_3$-alkyl; or a pharmacologically acceptable salt thereof.

8. A compound according to claim 7 wherein the compound is 3,4-dichloro-N-methyl-N-[2-(1-pyrrolidinyl)-4-(3-methoxypropyl)-3-cyclohexenyl]benzeneacetamide, or a pharmacologically acceptable salt thereof.

9. A compound according to claim 7 wherein the compound is 3,4-dichloro-N-methyl-N-[2-(1-pyrrolidinyl)-4-(3-methoxypropyl)cyclohexyl]-benzeneacetamide, or a pharmacologically acceptable salt thereof.

10. A composition useful in pharmaceutically effective dosage unit form for alleviating pain in warm-blooded animals which comprises a compound of claim 1 in combination with a pharmaceutically acceptable carrier.

11. A composition of claim 10 wherein the analgesically effective compound is a compound of the formula

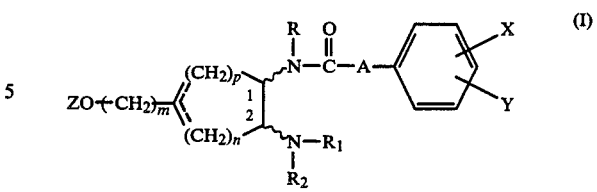

wherein p is 0, 1 or 2, n is 1, 2 or 3 so that the resulting cycloaliphatic ring containing them has six carbon atoms, m is 3 or 4;

A is —(CH$_2$)$_q$— wherein q is a whole number integer of from 0 to 1;

X and Y are independently hydrogen or halogen having an atomic number of from 9 to 35;

R is C$_1$ to C$_3$-alkyl;

R$_1$ and R$_2$ are taken together with the nitrogen to which they are bonded to complete a pyrrolidinyl ring;

Z is C$_1$ to C$_3$-alkanoyl, or a pharmacologically acceptable salt thereof.

12. A composition of claim 10 wherein the compound of formula (I) is 3,4-dichloro-N-methyl-N]2-(1-pyrrolidinyl)-3-(3-acetyloxypropyl)-3-cyclohexenyl]benzeneacetamide, or a pharmacologically acceptable salt thereof.

13. A method for alleviating pain in a warm-blooded animal which comprises administering to an animal suffering pain an analgesically effective amount of a compound of claim 1 in a pharmaceutical dosage unit form.

14. A method according to claim 13 wherein the analgesically effective compound is 3,4-dichloro-N-methyl-N-[2-(1-pyrrolidinyl)-3-(3-acetyloxypropyl)-3-cyclohexenyl]benzeneacetamide, or a pharmacologically acceptable salt thereof.

* * * * *